United States Patent [19]

Kunde

[11] Patent Number: 5,512,663

[45] Date of Patent: Apr. 30, 1996

[54] DISAZO REACTIVE DYESTUFFS

[75] Inventor: Klaus Kunde, Neunkirchen-Seelscheid, Germany

[73] Assignee: Bayer Aktiengesellschaft, Leverkusen, Germany

[21] Appl. No.: 231,527

[22] Filed: Apr. 22, 1994

[30] Foreign Application Priority Data

Apr. 30, 1993 [DE] Germany .................. 43 14 300.8

[51] Int. Cl.$^6$ ................ C09B 62/01; C09B 62/03; D06D 1/38

[52] U.S. Cl. .............. 534/633; 534/634; 534/635; 534/637; 8/549

[58] Field of Search .................. 534/623, 634, 534/637, 635

[56] References Cited

U.S. PATENT DOCUMENTS

| | | | |
|---|---|---|---|
| 2,993,038 | 7/1961 | Fasciati et al. | 534/637 |
| 5,288,294 | 2/1994 | Käser | 8/687 |

FOREIGN PATENT DOCUMENTS

| | | |
|---|---|---|
| 0534903 | 3/1993 | European Pat. Off. . |
| 1151625 | 7/1963 | Germany . |

OTHER PUBLICATIONS

6001 Chemical Abstracts, 115 (1991) Jul., 15, No. 2; CA#10841q: "Manufacture of C.I. Direct Blue 67", J. Baraniak et al.

*Primary Examiner*—Fiona T. Powers
*Attorney, Agent, or Firm*—William C. Gerstenzang; Sprung Horn Kramer & Woods

[57] ABSTRACT

Reactive dyestuffs, a process for their preparation and their use and novel intermediates and a process for their preparation.

Reactive dyestuffs of the formula (I)

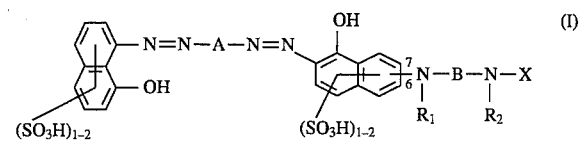

are described, in which

A denotes a radical of the formula

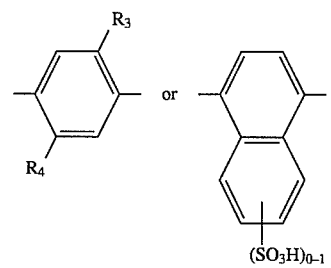

B denotes a bridging member, and $R_1$, $R_2$, $R_3$, $R_4$ and X have the meanings given in the description.

9 Claims, No Drawings

DISAZO REACTIVE DYESTUFFS

The invention relates to reactive dyestuffs which in the form of the free acid have the general formula (I)

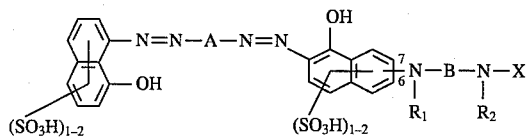

in which the radical

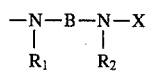

is attached to the 6 or 7 position of the naphthalene system, in which

A denotes a radical of the formula

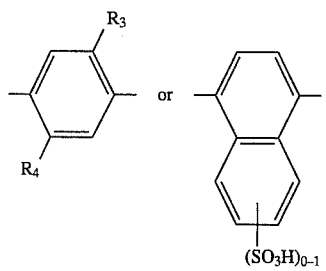

B denotes a bridging member, $R_1$ and $R_2$, independently of one another, denote H, substituted or unsubstituted $C_1$–$C_3$-alkyl, or substituted or unsubstituted phenyl, in particular sulphophenyl, examples of suitable substituents being OH, $SO_3H$, $CH_3$, $C_2H_5$, $OCH_3$, $OC_2H_5$ or $OC_3H_7$, or B, $R_1$ and $R_2$ together with the two nitrogen atoms form a substituted or unsubstituted piperazine, examples of suitable substituents being OH, $SO_3H$, $CH_3$, $C_2H_5$, $OCH_3$, $OC_2H_5$ or $OC_3H_7$, $R_3$ denotes H, $C_1$–$C_4$-alkyl, in particular $CH_3$, $C_1$–$C_4$-alkoxy, in particular $OCH_3$ or $OC_2H_5$, or $SO_3H$, $R_4$ denotes H, $C_1$–$C_4$-alkyl, in particular $CH_3$, $C_1$–$C_4$-alkoxy, in particular $OCH_3$ or $OC_2H_5$, and $NHCOCH_3$, $NHCONH_2$, $NHCOCH_2OH$, and X denotes a reactive system from the series consisting of 2,3-dichloroquinoxalines, pyrimidines or triazines, reactive dyestuffs of the formula (I) in which B denotes a sulpho-containing phenylene group and X denotes a 2-chloro-4-amino-1,3,5-triazine radical or a 2-chloro-4-sulphoanilino-1,3,5-triazine radical already disclosed in DE-A-1,151,625 (U.S. Pat. No. 2,993,038) being excepted.

Preference is given to dyestuffs of the formula (I), in which

X represents a triazine radical substituted by an amine which may contain a vinylsulphonyl group or a group which can be converted thereto under alkaline conditions or substituted by a diamine which is unsubstituted or substituted on the amine nitrogen not linked to the triazine radical with further reactive systems from the pyrimidine series, and the remaining substituents have the above meaning; furthermore, preference is given to dyestuffs which in the form of their free acid have the general formula (II)

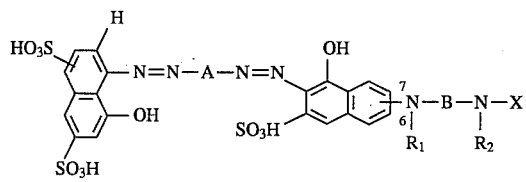

in which the radical

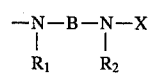

is attached to the 6 or 7 position of the naphthalene system, in which

A denotes a radical of the formula

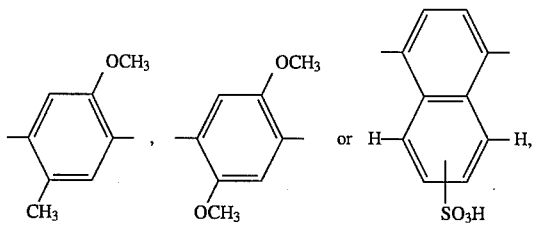

$R_1$ denotes H, $CH_3$ or $C_2H_4OH$, $R_2$ denotes H, $CH_3$, $C_2H_4OH$, $C_2H_4SO_3H$, $C_6H_5$ or $C_6H_4SO_3H$, or $R_1$ and $R_2$ together with B and the two N atoms form a piperazine, B denotes straight-chain or branched $C_2$–$C_6$-alkylene, $C_5$–$C_6$-cycloalkylene, phenylene which is unsubstituted or substituted by a sulpho group, a radical of the formula —$C_2H_4$—O—$C_2H_4$— or a radical of the formula

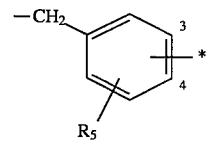

in which the group

is attached to the 3 or 4 position of the ring via the bond labelled with *, $R_5$ represents in particular H or $SO_3H$, and X has the abovementioned meaning, the exception made above also applying to the dyestuffs of the formula (II).

Particular preference is given to dyestuffs which in the form of their free acid have the general formula (III)

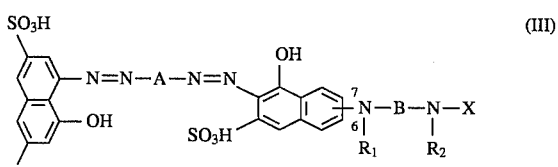

in which

B denotes $C_2H_4$, $C_3H_6$, $C_4H_8$ or a radical of the formula

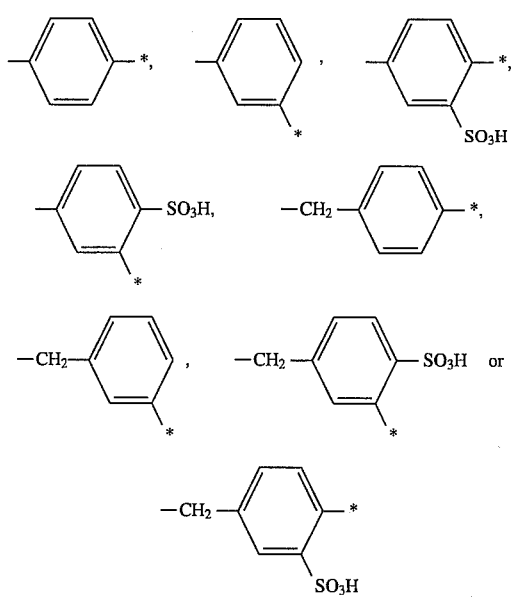

the group

being linked via the bond labelled with *,

X denotes a radical of a reactive system, in particular of the general formula

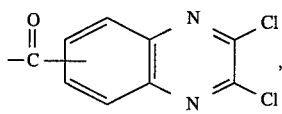 (IV)

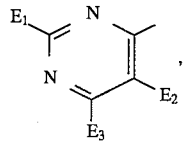 (Va)

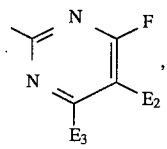 (Vb)

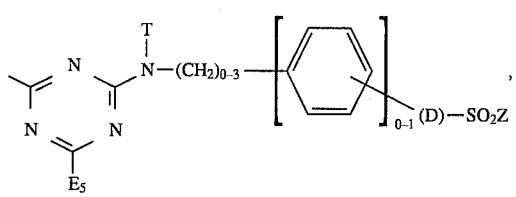 (VI)

 (VII)

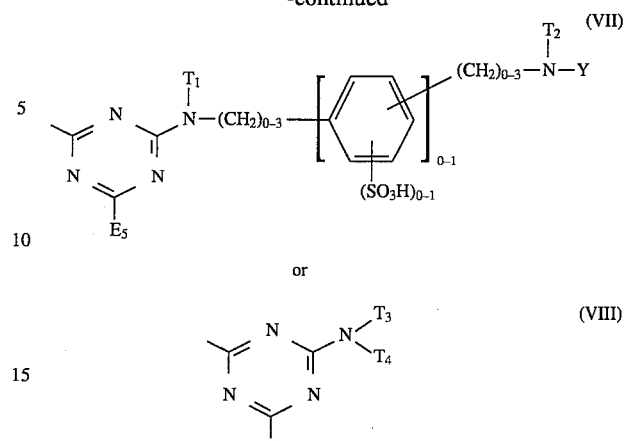

or (VIII)

in which $E_1$ represents H or F, $E_2$ represents H, Cl or CN, $E_3$ represents F or $CH_3$, $E_4$, $E_5$ represent F or Cl, T, $T_1$ denote H, substituted or unsubstituted $C_1$–$C_4$-alkyl, in particular $CH_3$ or $C_2H_5$, and $C_2H_4OH$ or substituted or unsubstituted phenyl, $T_2$ denotes H, substituted or unsubstituted $C_1$–$C_4$-alkyl, in particular $CH_3$ or $C_2H_5$, and $C_2H_4H$, $T_3$ denotes H, substituted or unsubstituted $C_1$–$C_4$-alkyl, in particular $C_2H_5OH$, optionally sulpho-containing phenyl, for example $C_6H_4SO_3H$ or $C_6H_3(SO_3H)_2$, $T_4$ denotes H, optionally substituted $C_1$–$C_4$-alkyl, in particular $CH_3$ or $C_2H_5$, and $C_2H_4OH$, it being possible for the substituted or unsubstituted $C_1$–$C_4$-alkyl radicals as T, $T_1$, $T_2$, $T_3$ and $T_4$ to be substituted, for example, by substituents such as OH, $OCH_3$, $OC_2H_5$ or $OC_2H_4OH$, D denotes an alkylene radical which may be interrupted by oxygen, in particular a radical of the formula $-(CH_2)_{1-6}-$ or $-C_2H_4-O-C_2H_4-$, Y denotes a radical of the formulae (Va) or (Vb), Z denotes $-CH=CH_2$ or a group which can be converted into vinylsulphonyl under alkaline conditions, in particular -$CH_2CH_2OSO_3H$ or $-CH_2CH_2Cl$, and A, $R_1$, $R_2$ have the abovementioned meanings.

Very particular preference is given to reactive dyestuffs of the formula (III) in which B denotes $C_2H_4$, $C_3H_6$, $C_4H_8$ or a radical of the formula

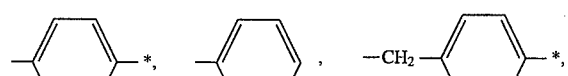

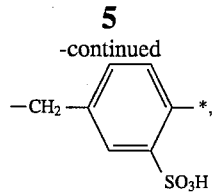

the group

being linked via the bond labelled with * and A, $R_1$, $R_2$ and X having the abovementioned meaning.

Furthermore, the invention provides a process for preparing reactive dyestuffs of the formula (I), which is characterized in that dyestuff bases of the general formula (IX)

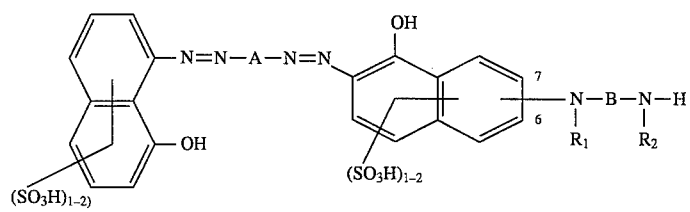

in which A, B, $R_1$ and $R_2$ have the abovementioned meanings and in which the radical

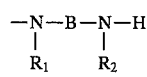

is attached to the 6 or 7 position of the naphthalene system, are reacted with reactive systems of the formula Hal-X, in which X has the abovementioned meaning, Hal represents halogen, in particular F or Cl and the dyestuffs excepted above are also excepted for the process.

Examples of reactive systems from the pyrimidine series which can be used are 5-chloro-2,4,6-trifluoropyrimidine, 5-chloro-4,6-difluoropyrimidine, 5-cyano-2,4,6-trifluoropyrimidine, 2,4,6-trifluoropyrimidine, 4,5,6-trifluoropyrimidine, 5-chloro-2,4,-difluoro-6-methylpyrimidine, examples of those from the quinoxaline series are 2,3-di-chloroquinoxaline-6-carbonyl chloride and of those from the triazine series are 2,4,6-trichloro-1,3,5-triazine or 2,4,6-trifluoro-1,3,5-triazine.

The dyestuff bases of the general formula (IX) can be obtained in particular by coupling diazonium compounds of the general formula

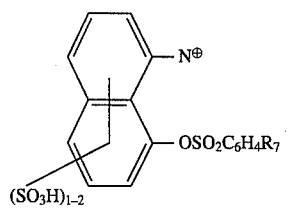

onto coupling components of the general formula

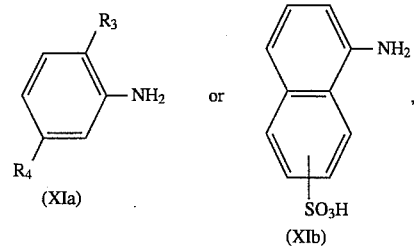

diazotizing the aminoazo compounds thus obtained on their part, and coupling these diazoniumazo compounds with coupling components of the general formula

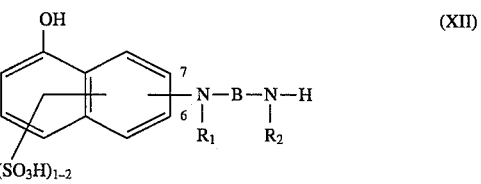

and hydrolyzing the disazo product of the formula (XIII) obtained

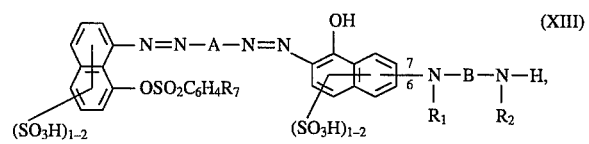

in which

A and B have the abovementioned meaning and $R_7$ denotes hydrogen, $C_1$-$C_4$-alkyl or halogen.

In a particular embodiment of this process, coupling components of the formula (XII) are used in which B, $R_1$ and $R_2$ have the meaning given under the novel dyestuff bases of the formula (IX).

Accordingly, the invention also relates to novel compounds of the formula (XIII) in which A and $R_7$ have the abovementioned meaning and B, $R_1$ and $R_2$ have the meaning given under the novel dyestuff bases of the formula (IX).

Diazonium compounds of the formula (X) are preferably obtained by diazotization of the O-benzenesulphonate of, for example, H-acid (1-amino-8-hydroxy-3,6-naphthalenedisulphonic acid), K-acid (1-amino-8-hydroxy-4,6-naphthalenedisulphonic acid), 5-amino-4-hydroxy-2-naphthalenesulphonic acid or 4-amino-5-hydroxy-1-naphthalenesulphonic acid.

Examples of coupling components of the formula (XIa) or (XIb) are aniline, 2-methoxyaniline, m-toluidine, 2-methoxy-5-methylaniline, 3-acetylaminoaniline, 2,5-dimethoxyaniline, 3-aminophenylurea, N-3-aminophenylglycolamide, 4-acetylamino-2-aminobenzenesulphonic acid, 1-aminonaphthalene, 5-amino-2-naphthalenesulphonic acid or 8-amino-2-naphthalenesulphonic acid.

The invention also provides novel dyestuff bases of the formula IX, in which A has the abovementioned meaning, $R_1$ represents H, $CH_3$ or $C_2H_4OH$, $R_2$ represents H, $CH_3$, $C_2H_4OH$, $C_2H_4SO_3H$, $C_6H_5$ or $C_6H_4SO_3H$, B denotes straight-chain or branched $C_2$–$C_6$-alkylene, $C_5$–$C_6$-cycloalkylene, a radical of the formula $-C_2H_4-O-C_2H_4-$ or a radical of the formula

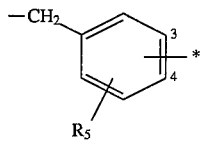

in which the group

is attached to the 3 or 4 position of the ring via the bond labelled with *, and $R_5$ represents H or $SO_3H$.

The invention also provides novel coupling components of the formula (XII), in which $R_1$ denotes H, $CH_3$ or $C_2H_4OH$, $R_2$ denotes H, $CH_3$, $C_2H_4OH$, $C_2H_4SO_3H$, $C_6H_5$ or $C_6H_4SO_3H$, $R_1$ and $R_2$ preferably having a different meaning, B denotes straight-chain or branched $C_2$–$C_6$-alkylene, preferably $C_3$–$C_6$-alkylene, $C_5$–$C_6$-cycloalkylene, a radical of the formula $-C_2H_4-O-C_2H_4-$ or a radical of the formula

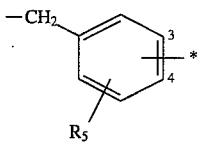

in which the group

is attached to the 3 or 4 position of the ring via the bond labelled with *, and $R_5$ represents H or $SO_3H$, with the proviso that $R_2 \neq$ hydrogen if B represents ethylene and $R_1$ represents hydrogen.

In a further embodiment, $R_2 \neq$ hydrogen if B represents propylene or butylene and $R_1$ represents hydrogen.

These coupling components according to the invention are preferably obtained by the Bucherer reactions of the corresponding aminohydroxynaphthalenesulphonic acids or dihydroxynaphthalenesulphonic acids of the general formula

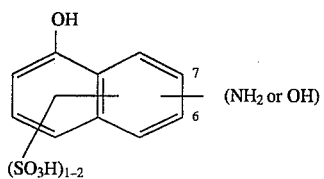

with diamines of the general formula $$H-N-B-N-H \qquad (XIV)$$
$$\phantom{H-}|\phantom{-B-}|$$
$$\phantom{H-}R_1\phantom{-B-}R_2$$

or monocarboxamides of the general formula $$H-N-B-N-COR \qquad (XIVa)$$
$$\phantom{H-}|\phantom{-B-}|$$
$$\phantom{H-}R_1\phantom{-B-}R_2$$

in which

R is an alkyl or aryl radical, for example $CH_3$, $C_2H_5$, $CH=CH-COOH$ or $C_6H_5$ and B, $R_1$ and $R_2$ have the meaning given above for the coupling components of the formula (XII) according to the invention.

If monoamides are used, the acyl radical is cleaved off after the Bucherer reaction under acidic or alkaline conditions.

Examples of starting compounds for the Bucherer reactions are J-acid (1-hydroxy-3-sulpho-6-aminonaphthalene), gamma-acid (1-hydroxy-3-sulpho-7-aminonaphthalene), 4,7-dihydroxy-2-naphthalenesulphonic acid, 2-amino-5-hydroxy-1,7-naphthalenedisuylphonic acid, 3-amino-5-hydroxy-2,7-naphthalenedisulphonic acid on the one hand and, on the other hand, examples are 1,2-diaminoethane, 1,2-diaminopropane, 1,3-diaminopropane, 1,4-diaminobutane, N,N'-dimethylethylenediamine, 1-(2'-hydroxyethylamino)-2-aminoethane, 2-(2'-aminoethylamino)-ethanesulphonic acid, 1,2-diaminocyclopentane, 1,2-diaminocyclohexane, 1,4-diaminocyclohexane, 1,3-diaminobenzene, 1,4-diaminobenzene, N-(3-methylaminophenyl)-acetamide, N-(4-methylaminophenyl)-acetamide, 2,4-diaminobenzenesulphonic acid, 2,5-diaminobenzenesulphonic acid, 4-aminomethylaniline, 3-aminomethylaniline, 4-methylaminomethylaniline, 3-methylaminomethylaniline, N-(4-aminomethylphenyl)-acetamide, N-(3-aminomethylphenyl)acetamide, N-(4-methylaminomethylphenyl)-acetamide, N-(3-methylaminomethylphenyl)-acetamide, 4-aminomethyl-2aminobenzenesulphonic acid, 4-aminomethyl-2-acetylaminobenzenesulphonic acid, 4-methylaminomethyl-2-acetylaminobenzenesulphonic acid, 5-aminomethyl-2-aminobenzenesulphonic acid, 5-aminomethyl-2-acetylaminobenzenesulphonic acid, 5-methylaminomethyl-2-acetylaminobenzenesulphonic acid, piperazine.

The conditions of the Bucherer reaction are known per se and described, for example, in GB-A-230,457; it is preferably carried out in water at temperatures of between 80° C. and 130° C. preferably between 100° and 130° C. the diamine or the amide preferably being used in excess.

The process will be illustrated by the following examples:

A)

23.9 g of J-acid, 14 g of N,N'-dimethylethylenediamine and 20.8 g of sodium bisulphite are dissolved in 200 ml of water at a pH of 6, and the mixture is heated at 100° C. for 10 hours. The product of the formula

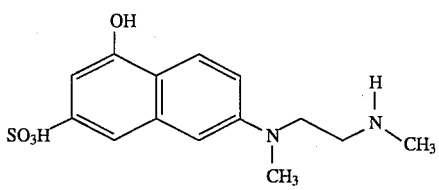

precipitates upon cooling, is isolated, washed with saturated sodium chloride solution and dried.

The NMR spectrum (250 MHz, (dimethyl sulphoxide)-$d_6$) exhibits the following signals: δ=2.55 s, 3H; δ=2.94 s, 3H; δ=3.08 m, 2H; δ=3.4 m, 1H; δ=3.66 m, 2H; δ=6.88 d, 1H; δ=6.94 d, 1H; δ=7.12 q, 1H; δ=7.47 d, 1H; δ=7.91 d, 1H; δ=9.8 broad s, 1H.

B)

23.9 g of J-acid, 16 g of 1-hydroxyethylamino-2-aminoethane and 20.8 g of sodium bisulphite were dissolved in 200 ml of water at a pH of 6, and the mixture was heated at 100° C. for 10 hours. The product of the formula

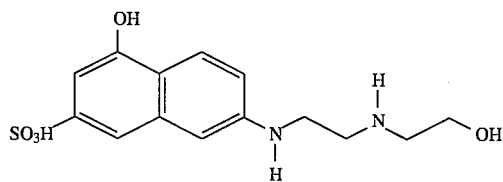

precipitates upon cooling, is isolated, washed with saturated sodium chloride solution and dried.

The NMR spectrum (250 MHz, (dimethyl sulphoxide)-$d_6$) exhibits the following signals: δ=3.09 m, 2H; δ=3.14 m, 2H; δ=3.44 m, 2H; δ=3.68 m, 2H; δ=5.29 broad m, 1H; δ=6.03 broad t, 1H; δ=6.82 s, 1H; δ=6.9 m, 2H; δ=7.45 s, 1H; δ=7.96 d, 1H; δ=8.5 broad m, 2H; δ=9.9 broad s, 1H.

The process for preparing the dyestuff bases of the formula (IX) is known per se; it is analogous to the process for preparing C.I. Direct Blue 67.

Diazotization and coupling are preferably carried out in aqueous medium at temperatures of between 0° C. and 30° C., and alkaline hydrolysis of the benzenesulphonate ester is preferably carried out at temperatures of between 80° C. and 110° C.

In the process according to the invention for preparing dyestuffs of the formula (I), triazines can be reacted, before or after condensation with the dyestuff base, with ammonia, aliphatic, aromatic or araliphatic amines which may additionally contain a vinylsulphonyl radical or a group which can be converted to such a radical by treatment with alkalis, such as a 2-sulphatoethylsulphonyl or a 2-chloroethylsulphonyl group, or be reacted with aliphatic, aromatic or araliphatic diamines which are linked at an amine nitrogen to a reactive system from the pyrimidine series, such as listed, for example, above.

Examples of such amines are 2-aminoethanol, 2-methylantinoethanol, 2-ethylaminoethanol, aniline, N-methylaniline, N-ethylaniline, N-2-hydroxyethylaniline, 2-aminoethyl 2'-sulphatoethyl sulphone, 3-aminopropyl 2'-sulphatoethyl sulphone, 2-(2-aminoethoxy)ethyl 2"-sulphatoethyl sulphone, 4-aminobutyl 2'-sulphatoethyl sulphone, 4-aminophenyl 2'-sulphatoethyl sulphone, 4-methylaminophenyl 2'-sulphatoethyl sulphone, 3-aminophenyl 2'-sulphatoethyl sulphone, 3,-methylaminophenyl 2'-sulphatoethyl sulphone, 3-aminobenzyl 2'-sulphatoethyl sulphone, 4-aminobenzyl 2'-sulphatoethyl sulphone, 2-phenylaminoethyl 2'-sulphatoethyl sulphone, 3-phenylaminoethyl 2'-sulphatoethyl sulphone; examples of such diamines are the ones mentioned above as components of the Bucherer reaction, if desired after hydrolysis of the acetylamino group.

The condensations of the amino groups of the starting components with the reactive systems are carried out, independently of the order, in aqueous or aqueous organic media in the presence of acid-binding agents. Depending on the nature of the starting components, the first step of the condensation is carried out in pH ranges from 2 to 8, preferably 3 to 7, and at temperatures from 0° to 60° C., preferably from 0° to 40° C. The exchange of the second halogen atom of the triazine is carried out in a pH range from 4 to 10, preferably from 5 to 9, and in a temperature range from 0° to 60° C., preferably 0° to 30° C.

Examples of acid-binding agents are carbonates, hydroxides or phosphates, such as sodium carbonate, sodium bicarbonate, dilute sodium hydroxide solution, di- or trisodium phosphate or sodium fluoride.

If the condensation or the dyestuff synthesis is desired to lead directly to a dyestuff solution or to a liquid dyestuff preparation, the use of lithium carbonates or lithium hydroxide may be advantageous, if appropriate together with solubilizers and/or stabilizing buffer systems.

The reactive dyestuffs of the formula (I) can be isolated and processed to give dry dyestuff preparations. Isolation preferably takes place at the lowest possible temperatures by salting out and filtration. The filtered dyestuffs can be dried, if desired after addition of diluents and/or buffering agents, for example after addition of a mixture of equal parts of mono- and di-sodium phosphate; preferably, drying is carried out at moderately high temperatures and under reduced pressure.

In certain cases, the dry preparations according to the invention can be prepared directly, i.e., without intermediate isolation of the dyestuffs, by spray-drying of the preparation mixture.

The formulae given are those of the free acids. The preparation in general gives salts, in particular the alkali metal salts, such as sodium salts, potassium salts or lithium salts. The dyestuffs can also be used as concentrated solutions.

The dyestuffs according to the invention are highly suitable for dyeing and printing natural and synthetic OH- or amido-containing materials, in particular those made of cellulose and polyamides. They are particularly suitable for dyeing cellulose materials by the exhaust and cold pad-batch methods, and for printing cotton and staple viscose.

Dyeings having good general fastness properties, in particular good wetfastness properties, in combination with good build-up properties and high fixation yields are obtained.

Textile products containing hydroxyl- or amido-containing materials dyed with dyestuffs of the formula (I)—with the exception of the dyestuffs excepted above—are also according to the invention.

EXAMPLES

Example 1

45.9 g of the O-benzenesulphonate of H-acid are diazotized in water at 0° C. with 6.9 g of sodium nitrite. The resulting diazonium compound is coupled onto 13.7 g of 2-methoxy-5-methylaniline at a pH of 2.5 and at 30° C. The aminoazo compound is diazotized at 10° C. with 6.9 g of sodium nitrite. The diazonium compound is coupled onto 28.2 g of 7-(2'-aminoethylamino)-4-hydroxy-2-naphthalenesulphonic acid at a pH of 7 and at 20° C. The benzenesulphonyl radical is cleaved off at a pH of 12 and 90° C. The dyestuff base of the formula

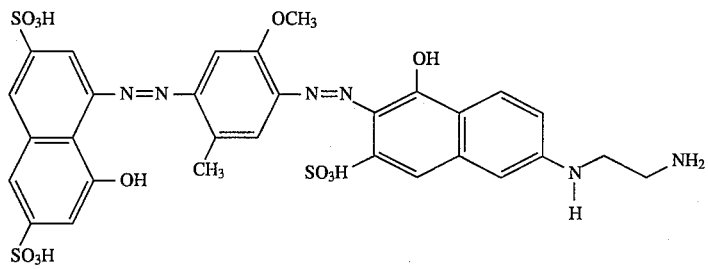

is isolated.

30.4 g of 2-amino-1,4-benzenedisulphonic acid are condensed in water with 17.2 g of 2,4,6-trifluoro-1,3,5triazine at a pH of 4 and 0° C. The solution of this condensation product is added to a suspension of the dyestuff base in water.

The second condensation on the triazine is carried out at pH 7.5 and 40° C. The dyestuff is precipitated with sodium chloride, isolated and dried at 40° C. in vacuo and has the formula dyestuff is precipitated with sodium chloride, isolated and dried at 40° C. in vacuo and has the formula (a)

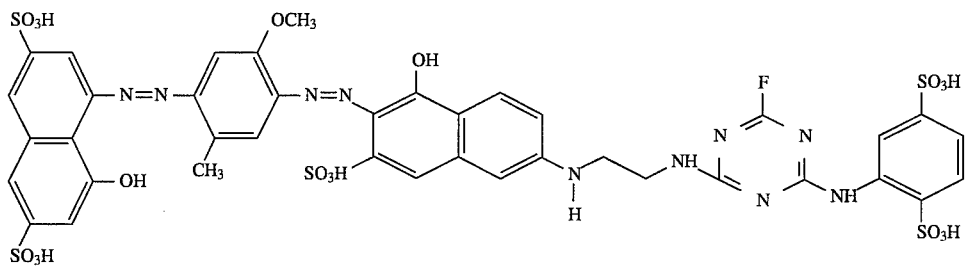

It produces blue dyeings on cotton and viscose.

Example 2

4.5 g of the O-benzenesulphonate of H-acid are diazotized in water at 0° C. with 6.9 g of sodium nitrite. The diazonium compound is coupled onto 22.3 g of 8-amino-2-naphthalenesulphonic acid at pH 6 and 20° C. The amino-azo compound is diazotized with 0.9 g of sodium nitrite at 20° C. The diazonium compound is coupled onto 32.6 g of 7-[2-(2'-hydroxyethylamino)-ethylamino]-4-hydroxy-2-naphthalenesulphonic acid at pH 7 and 20° C. The benzenesulphonyl radical is cleaved off at pH 12 and 50° C. The dyestuff base of the formula (b)

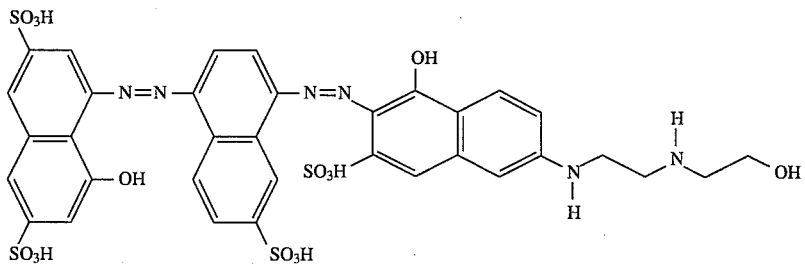

is isolated, resuspended in water and condensed with 18 g of 5-chloro-4,6-difluoropyrimidine at pH 7.5 and 40° C. The

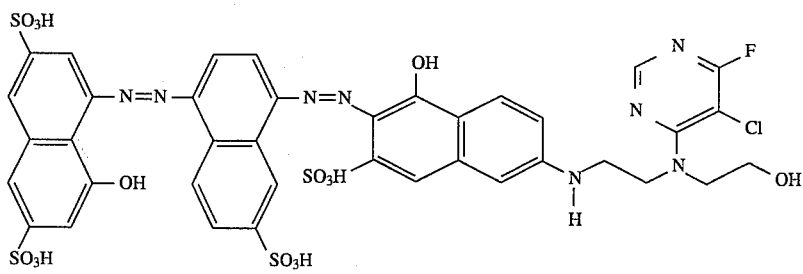

It produces blue dyeings on cotton and viscose.

Example 3

45.9 g of the O-benzenesulphonate of H-acid are diazotized in water at 0° C. with 6.9 g of sodium nitrite. The resulting diazonium compound is coupled onto 22.3 g of 5-amino-2-naphthalenesulphonic acid at pH 6 and 20° C. The aminoazo compound is diazotized at 20° C. with 6.9 g of sodium nitrite. The diazonium compound is coupled onto 30.8 g of 7-(1-piperazinyl)-4-hydroxy-2-naphthalenesulphonic acid at pH 7 and 20° C. The benzenesulphonyl radical is cleaved off at pH 12 and 50° C. The dyestuff base of the formula The reaction of the dyestuff base with the reactive system takes place at pH 7 and 40° C.

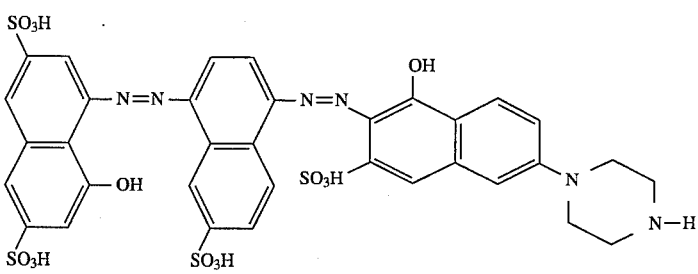

(c)

is isolated.

38.7 g of 2-phenylaminoethyl 2'-sulphatoethyl sulphone are condensed in water at pH 7 and 0° C. with 22.2 g of 2,4,6-trichloro-1,3,5-triazine. The solution of this condensation product is added to a suspension of the dyestuff base in water. The second condensation on the triazine is carried out at pH 7.5 and 40° C. The dyestuff is precipitated with sodium chloride, isolated and dried at 40° C. in vacuo and has the formula

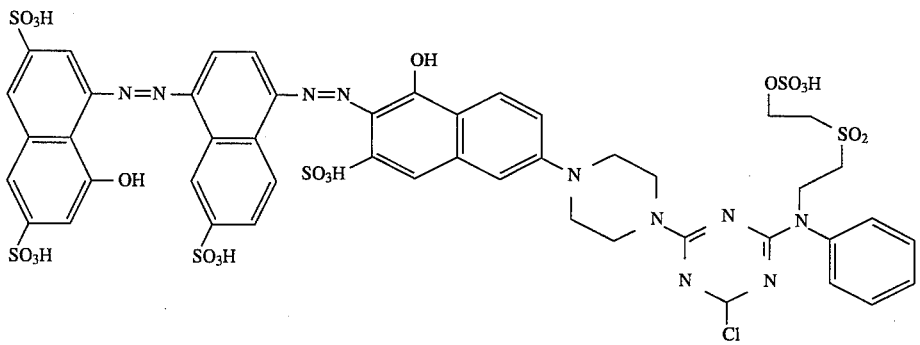

It produces blue dyes on cotton and viscose.

Further dyestuffs which produce blue dyeings on cotton and viscose are listed in the table below.

TABLE 1

| Ex. No. | 1st diazonium compound | 1st coupling component | 2nd coupling component | Reactive system |
|---|---|---|---|---|
| 4 | (structure) | (structure) | (structure) | (structure) |
| 5 | (structure) | (structure) | (structure) | (structure) |
| 6 | (structure) | (structure) | (structure) | (structure) |
| 7 | (structure) | (structure) | (structure) | (structure) |

TABLE 1-continued

| Ex. No. | 1st diazonium compound | 1st coupling component | 2nd coupling component | Reactive system |
|---|---|---|---|---|
| 8 | | | | |
| 9 | | | | |
| 10 | | | | |
| 11 | | | | |

TABLE 1-continued

| Ex. No. | 1st diazonium compound | 1st coupling component | 2nd coupling component | Reactive system |
|---|---|---|---|---|
| 12 | | | | |
| 13 | | | | |
| 14 | | | | |
| 15 | | | | |

TABLE 1-continued

| Ex. No. | 1st diazonium compound | 1st coupling component | 2nd coupling component | Reactive system |
|---|---|---|---|---|
| 16 | | | | |
| 17 | | | | |
| 18 | | | | |
| 19 | | | | |

TABLE 1-continued

| Ex. No. | 1st diazonium compound | 1st coupling component | 2nd coupling component | Reactive system |
|---|---|---|---|---|
| 20 | | | | |
| 21 | | | | |
| 22 | | | | |
| 23 | | | | |

TABLE 1-continued

| Ex. No. | 1st diazonium compound | 1st coupling component | 2nd coupling component | Reactive system |
|---|---|---|---|---|
| 24 | (naphthalene with N:N(+), SO₃H, OSO₂-phenyl, SO₃(−)) | 8-amino-naphthalene-2-sulfonic acid (NH₂, SO₃H) | 8-hydroxy-6-sulfo-2-(2-aminoethylamino)naphthalene | 3-[N-(4,6-difluoropyrimidin-2-yl)amino]phenyl-CH₂-SO₂-CH₂CH₂-OSO₃H |
| 25 | (naphthalene with N:N(+), SO₃H, OSO₂-phenyl, SO₃(−)) | 2-methoxy-5-methylaniline (OCH₃, NH₂, CH₃) | 8-hydroxy-6-sulfo-2-(2-aminoethylamino)naphthalene | 2-chloro-4,6-difluoropyrimidine |
| 26 | (naphthalene with N:N(+), SO₃H, OSO₂-phenyl, SO₃(−)) | 8-amino-naphthalene-2-sulfonic acid (NH₂, SO₃H) | 8-hydroxy-6-sulfo-2-[N-methyl-N-(2-methylaminoethyl)amino]naphthalene | 2,4,6-trifluoropyrimidine |

TABLE 1-continued

| Ex. No. | 1st diazonium compound | 1st coupling component | 2nd coupling component | Reactive system |
|---|---|---|---|---|
| 27 | | | | |
| 28 | | | | |

Example 29

89 g of the dyestuff base from Example 2 (formula b) are dissolved in water and condensed with 18.5 g of cyanuric chloride at pH 7 and 0° C. 38.7 g of 2-phenylaminoethyl 2'-sulphatoethyl sulphone are added to the resulting solution; the second condensation on the triazine is carried out at pH 7.5 and 40° C. The dyestuff is salted out with sodium chloride, isolated and dried at 40° C. in vacuo and has the formula

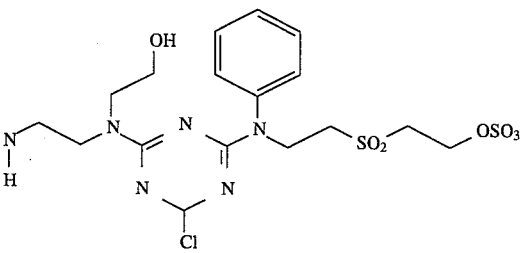

It produces blue dyeings on cotton and viscose.

I claim:

1. A reactive dyestuff which in the form of the free acid has the formula

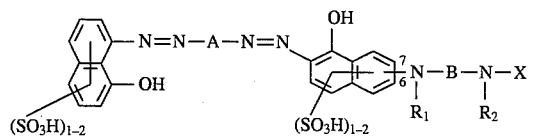

in which the radical

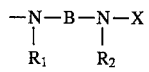

is attached to the 6 or 7 position of the naphthalene system, in which

A denotes a radical of the formula

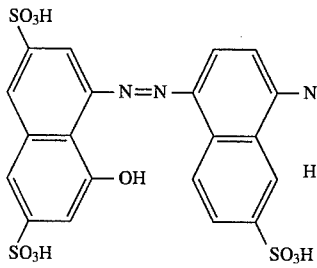

B denotes straight-chain or branched $C_2$–$C_6$-alkylene, $C_5$–$C_6$-cycloalkylene, a radical of the formula —$C_2H_4$—O—$C_2H_4$— or a radical of the formula

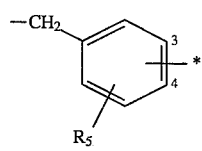

in which the group

is attached to the 3 or 4 position of the ring via the bond labelled with *, and $R_5$ represents H or $SO_3H$, $R_1$ and $R_2$, independently of one another, denote H, substituted or unsubstituted $C_1$–$C_3$-alkyl, or substituted or unsubstituted phenyl, or B, $R_1$ and $R_2$ together with the two nitrogen atoms form a substituted or unsubstituted piperazine, $R_3$ denotes H, $C_1$–$C_4$-alkyl, $C_1$–$C_4$-alkoxy or $SO_3H$, $R_4$ denotes H, $C_1$–$C_4$-alkyl, $C_1$–$C_4$-alkoxy, $NHCOCH_3$, $NHCONH_2$ or $NHCOCH_2OH$, and X denotes a reactive system from the series consisting of 2,3-dichloroquinoxalines, pyrimidines or triazines.

2. The reactive dyestuff according to claim 1, wherein

X represents a triazine radical substituted by an amine which is unsubstituted or substituted by a vinylsulphonyl group or a group which can be converted thereto under alkaline conditions or substituted by a diamine which is unsubstituted or substituted on the amine nitrogen not linked to the triazine radical with further reactive systems from the pyrimidine series.

3. The reactive dyestuff according to claim 1, wherein in the form of the free acid it has the formula

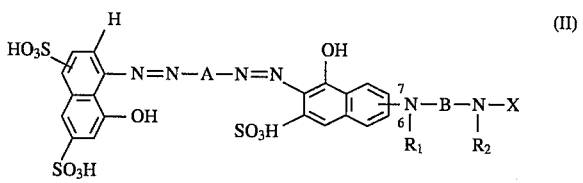

in which

A denotes a radical of the formula

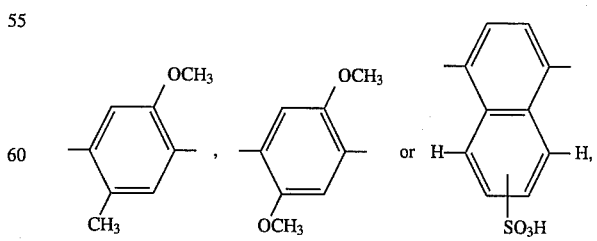

$R_1$ denotes H, $CH_3$ or $C_2H_4OH$, $R_2$ denotes H, $CH_3$, $C_2H_4OH$, $C_2H_4SO_3H$, $C_6H_5$ or $C_6H_4SO_3H$, or $R_1$ and $R_2$ together with B and the two N atoms form a piperazine.

4. The reactive dyestuff according to claim 1, wherein in the form of its free acid it has the formula

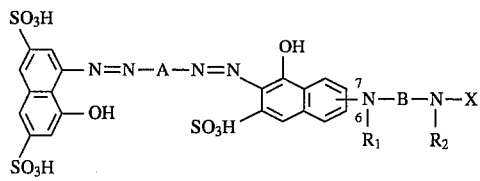

(III)

in which

B denotes $C_2H_4$, $C_3H_6$, $C_4H_8$ or a radical of the formula

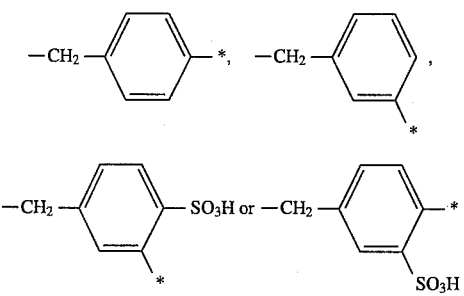

the group

being linked via the bond labelled with *,

X denotes a radical of the general formula

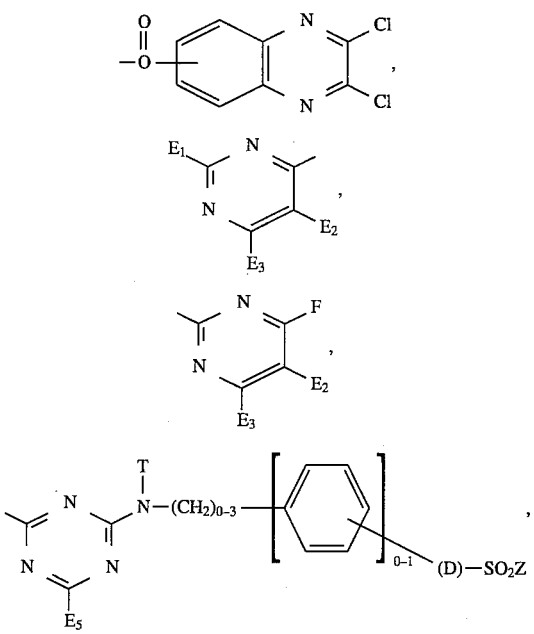

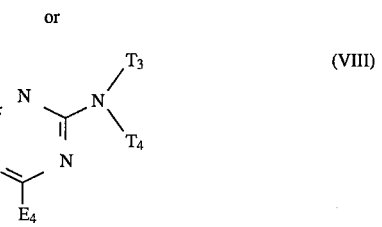

(VII)

or

(VIII)

in which $E_1$ represents H or F, $E_2$ represents H, Cl or CN, $E_3$ represents F or $CH_3$, $E_4$, $E_5$ represents F or Cl, T, $T_1$ denote H, substituted or unsubstituted $C_1$–$C_4$-alkyl, or substituted or unsubstituted phenyl, $T_2$ denotes H, substituted or unsubstituted $C_1$–$C_4$-alkyl, $T_3$ denotes H, substituted or unsubstituted $C_1$–$C_4$-alkyl, or phenyl which is unsubstituted or substituted by sulfo, $T_4$ denotes H, or substituted or unsubstituted $C_1$–$C_4$-alkyl, D denotes a radical of the formula —$(CH_2)_{1-6}$— or —$C_2H_4$—O—$C_2H_4$—, Y denotes a radical of the formulae (Va) or (Vb), Z denotes —CH=$CH_2$ or a group which can be converted into vinylsulphonyl under alkaline conditions.

5. A process for dyeing or printing natural or synthetic hydroxyl- or amido-containing materials by applying thereto a reactive dyestuff according to claim 1.

6. Textile products containing hydroxyl- or amido-containing materials dyed with a dyestuff according to claim 1.

7. A reactive dyestuff wherein in the form of its free acid it has the formula

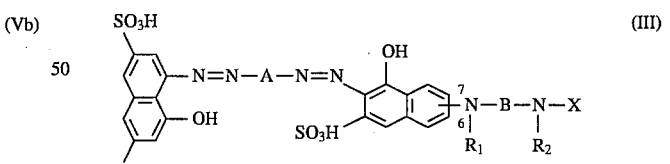

(III)

in which the radical

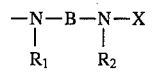

is attached to the 6 or 7 position of the naphthalene system, in which

A denotes a radical of the formula

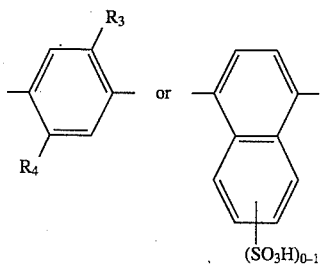

B denotes a radical of the formula

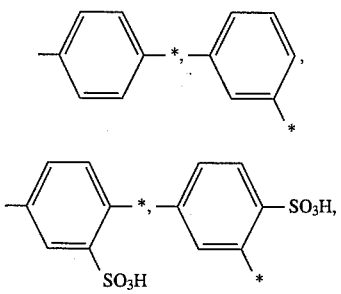

the group

being linked via the bond labelled with *, $R_1$ and $R_2$, independently of one another, denote H, substituted or unsubstituted $C_1$-$C_3$-alkyl, or substituted or unsubstituted phenyl, $R_3$ denotes H, $C_1$-$C_4$-alkyl, $C_1$-$C_4$-alkoxy or $SO_3H$, $R_4$ denotes H, $C_1$-$C_4$-alkyl, $C_1$-$C_4$-alkoxy, $NHCOCH_3$, $NHCONH_2$ or $NHCOCH_2OH$, and X denotes a radical of the general formula

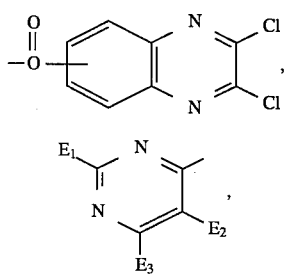

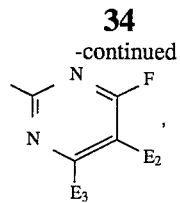

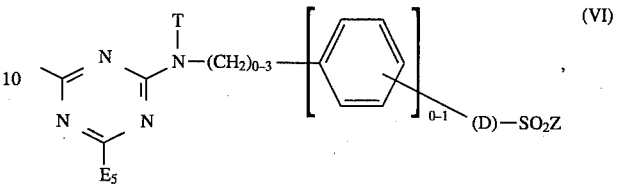

or

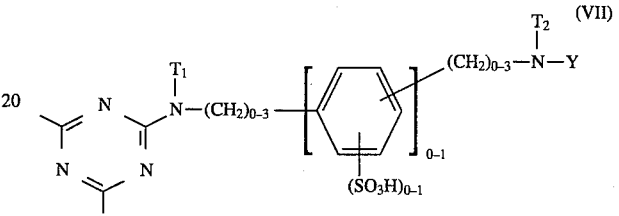

in which $E_1$ represents H or F, $E_2$ represents H, Cl or CN, $E_3$ represents F or $CH_3$, $E_4$, $E_5$ represents F or Cl, T, $T_1$ denote H, substituted or unsubstituted $C_1$-$C_4$-alkyl, or substituted or unsubstituted phenyl, $T_2$ denotes H, substituted or unsubstituted $C_1$-$C_4$-alkyl, $T_3$ denotes H, substituted or unsubstituted $C_1$-$C_4$-alkyl, or phenyl which is unsubstituted or substituted by sulfo, $T_4$ denotes H, or substituted or unsubstituted $C_1$-$C_4$-alkyl, D denotes a radical of the formula —$(CH_2)_{1-6}$— or —$C_2H_4$—O—$C_2H_4$—, Y denotes a radical of the formulae (Va) or (Vb), Z denotes —CH=$CH_2$ or a group which can be converted into vinylsulphonyl under alkaline conditions.

8. A process for dyeing or printing natural or synthetic hydroxyl- or amido-containing materials by applying thereto a dyestuff according to claim 7.

9. Textile products containing hydroxyl- or amido-containing materials dyed with a dyestuff according to claim 7.

* * * * *

UNITED STATES PATENT AND TRADEMARK OFFICE
CERTIFICATE OF CORRECTION

PATENT NO. : 5,512,663
DATED : April 30, 1996
INVENTOR(S) : Kunde, Klaus

It is certified that error appears in the above-indentified patent and that said Letters Patent is hereby corrected as shown below:

Col. 30, line 33    Delete " series " and substitute -- group --

Signed and Sealed this

Twenty-ninth Day of October 1996

Attest:

BRUCE LEHMAN

Attesting Officer    Commissioner of Patents and Trademarks